United States Patent [19]
Schutz et al.

[11] Patent Number: 5,214,210
[45] Date of Patent: * May 25, 1993

[54] CATALYST AND PROCESS FOR MAKING ANILINE FROM PHENOL

[75] Inventors: Alain A. Schutz, Penn Township, Westmoreland County; Leonard A. Cullo, Greensburg, both of Pa.

[73] Assignee: Aristech Chemical Corporation, Pittsburgh, Pa.

[*] Notice: The portion of the term of this patent subsequent to Feb. 22, 2009 has been disclaimed.

[21] Appl. No.: 755,222

[22] Filed: Sep. 5, 1991

[51] Int. Cl.$^5$ .......................................... C07C 209/18
[52] U.S. Cl. ..................................... 564/402; 502/355
[58] Field of Search ................ 502/231, 355, 415; 564/402

[56] References Cited

U.S. PATENT DOCUMENTS

| | | |
|---|---|---|
| 1,935,209 | 11/1933 | Herold et al. .................... 260/130.5 |
| 2,968,676 | 1/1961 | Potter, Jr. et al. .................. 260/576 |
| 3,272,865 | 9/1966 | Barker .................................. 260/581 |
| 3,860,650 | 1/1975 | Becker et al. ..................... 260/570 D |
| 4,987,260 | 1/1991 | Yasuhara et al. .................... 564/402 |
| 5,091,579 | 2/1992 | Cullo .................................. 564/402 |

FOREIGN PATENT DOCUMENTS 127396 12/1984 European Pat. Off. .
293483 12/1988 European Pat. Off. .

OTHER PUBLICATIONS

LaRoche Chemicals Product Bulletin, "Versal B", Oct. 1, 1990.

*Primary Examiner*—Glennon H. Hollrah
*Assistant Examiner*—B. M. Born
*Attorney, Agent, or Firm*—William L. Krayer

[57] ABSTRACT

Phenolic compounds, particularly phenol, are aminated by reaction with ammonia in the presence of a catalyst made by calcining bayerite.

7 Claims, No Drawings

CATALYST AND PROCESS FOR MAKING ANILINE FROM PHENOL

TECHNICAL FIELD

This invention pertains to a catalyst for the manufacture of aromatic amines by the vapor phase reaction of phenols with ammonia. In particular, it relates to high activity alumina catalysts made by calcining bayerite, a crystalline aluminum hydroxide.

BACKGROUND OF THE INVENTION

The reaction of phenol and ammonia in vapor phase over acid catalysts has been described as early as 1933 in U.S. Pat. No. 1,935,209. A series of relevant patents has evolved, including U.S. Pat. Nos. 2,013,873, 3,272,865, and 3,578,714. A process flowsheet was published by M. Becker et al (Chemical Engineering, Apr. 2, 1973, pp 42–43) describing a process for making aniline by the reaction of phenol with an excess of ammonia over a catalyst made up of aluminas derived from precipitated gels containing less than 1% alkali metal and having surface areas of more than 150 sq. meters per gram.

The commercialization of this process resulted from two discoveries which are described in U.S. Pat. Nos. 3,860,650 and 3,682,782. The '782 patent describes the recovery of high purity aniline from aniline-phenol mixtures. Crude aniline containing low residual phenol is needed, as phenol and aniline have close boiling points and also form an azeotrope. Such crude is obtained at low LHSV over a high activity catalyst. The '650 patent describes the catalytic part of the process which is carried out over acid washed H-151 alumina, manufactured by Alcoa (Activated and Catalytic Aluminas, Brochure published by Alcoa Chemicals, Oct. 1, 1961), a desiccant alumina derived from a precipitated gel.

The '650 patent describes also the procedure of leaching H-151 with aqueous acid solutions to remove sodium, which is imperative for achieving relatively high catalytic activity. Even though both disclosures permitted successful commercialization, this process is still an unusual vapor phase catalytic technology in that LHSV is adjusted at about 0.04 and an ammonia to phenol mole ratio of about 20 is needed to obtain high phenol conversion and high selectivities to aniline. Higher LHSV which would require higher reaction temperatures are not desirable because of ammonia dissociation to nitrogen and hydrogen. However, low capital costs, the low catalyst deactivation and minimum waste disposal problems are attractive compared to the conventional route of making aniline and, more generally, aromatic amines, from nitrobenzenes. As an environmental matter, a process which does not generate nitrogen oxide compounds is of increasing interest.

Following the implementation of the process, it appeared to the inventors herein that acid washed H-151 alumina is an exceptional catalyst in many ways and attempts to obtain a similar catalyst having at least equivalent activity, selectivity deactivation rate and thermal stability failed for the following reasons:

Silico-alumina catalysts have higher acid strength and produce undesirable by-products. Side reactions also favor the deposit of carbonaceous materials the catalyst which results in high deactivation rates. Such catalysts are described in U.S. Pat. No. 3,272,865.

Binary oxides such as zirconia-alumina, titania-alumina and others reported in Japanese Patents 23,053 and 23,571 are not as active as the acid leached H-151 alumina and deactivate rapidly because of the need of high reaction temperatures.

European Patent 293,483 describes a low alkali alumina catalyst obtained by firing an alumina (H-152 manufactured by Alcoa) at a temperature of 600°–900° C. followed by acid treatment. Although the catalyst shows good catalytic stabilities, its activity is about 70% of the H-151 based catalyst; equivalent performances are obtained at reaction temperatures of about 375° C. compared to 363° C. for the acid leached H-151. The firing treatment is needed to expel the sodium out of the alumina structure which then becomes removable by acid leaching treatments. However, while the removal of sodium is beneficial to the catalytic activity, the calcination at high temperature causes the alumina crystallites to sinter. The surface area, and consequently the catalytic activity are relatively reduced.

Other aluminas such as those obtained by calcination of gibbsite (product of the Bayer process) also contain appreciable amounts of sodium. Although high surface area can be obtained, the sodium is usually difficult to remove. Intensive acid treatments are able to bring the sodium content down to 0.3% $Na_2O$ but reduce the surface area dramatically. A comparative example is shown in this disclosure.

Gamma aluminas obtained by calcination of pseudo-boehmite materials such as Catapal (Vista Chemicals), Disperal and Pural (Condes Chemie), made from aluminum, and Versal 250, 450, 800 and 900 (LaRoche Chemicals), made from sodium aluminate, are low sodium aluminas. Comparative example D of U.S. Pat. No. 3,860,650 reported the test reaction results of such catalysts. It is shown that a reaction temperature of about 410° C. is necessary to obtain 95% phenol conversion. Two disadvantages of such catalysts are their relatively lower surface areas and packed densities.

It is an object of this invention to provide a catalytic process for converting phenols to aromatic amines and in particular phenol to aniline.

It is a further object of this invention to provide a catalyst comparable in activity to one made from the acid leached H-151 alumina.

It is also an object of this invention to provide a catalyst which can be made cheaply and relatively easily with commercially available raw materials.

It is also a further object to provide a method for manufacturing such catalyst with good mechanical properties.

DETAILED DESCRIPTION OF THE INVENTION

This invention provides a process for making aromatic amines from phenols and ammonia over alumina catalysts made primarily from bayerite, a pure crystalline aluminum trihydroxide. Such material is described in Alcoa Technical Paper No. 19 written by Karl Wefers and Gordon M. Bell in 1972 which is incorporated herein by reference. In particular, this invention relates to alumina catalysts, useful for converting phenol to aniline, made from crystalline aluminum compounds containing at least 70% Versal B (trademark for a bayerite manufactured by LaRoche Chemicals, formerly Kaiser Chemicals) or similar bayerite.

This discovery that bayerite can be treated to prepare a useful aniline catalyst is surprising in view of earlier results obtained with aluminas made from crystalline aluminum trihydroxides. While U.S. Pat. No. 3,860,560 describes the use of catalyst made from precipitated alumina gels, and states (page 3, lines 7-10) "the non-gel aluminas have consistently demonstrated less favorable performance characteristics than are obtained with the precipitated gels", it has been found unexpectedly that similar activities can be obtained with alumina catalysts derived from a non-gel alumina such as bayerite. Experiments conducted with catalysts made with other aluminum trihydroxide such as gibbsite did not provide the same performances.

The major differences between the gel alumina, gibbsite and bayerite are the crystal structure and the size of the individual crystallites but all three are made from sodium aluminate. After calcination at about 400°-600° C., these aluminum hydroxides are converted to their respective transition alumina. Gibbsite is transformed to chi alumina, bayerite to eta alumina and alumina gel, being amorphous pseudoboemite, to gamma alumina. The catalysts made with these materials then have quite distinctive structures.

The crystal sizes of the aluminum hydroxide compounds differ considerably and affect the catalyst performance because of the following:

Gibbsite usually crystallizes into large crystals with substantial amount of sodium integrated into the structure. Such typical gibbsite is produced in the Bayer process. Sodium is consequently difficult to remove even after calcination and reduces considerably the catalytic activity of the alumina. The pore structure of the calcined gibbsite is mainly constituted of micropores created by a network of submicroscopic cracks and crevices in the crystals. Such pore structure, upon subsequent heat treatment, collapses faster than the one obtained from finely divided particles such as the one of gamma alumina. This results in relatively lower surface areas when the material is calcined at temperatures about 600° C.

In contrast to gibbsite, bayerite does not crystallize into large individual monocrystals but into small somatoids of high purity. Although there is a close similarity in the thermal decomposition of bayerite and gibbsite, the purity and the crystallite size of bayerite leads to better catalytic materials.

A general procedure for making the catalyst of the present invention is as follows: bayerite is mixed with about 10% to about 60% (based on the bayerite) deionized water, up to about 25% pseudoboehmite or other low-sodium alumina, and preferably about 1% to about 5% nitric or other acid. Spheres or other solid particles are made from this mix as known in the art and then calcined at 400° to 600° C. for at least about an hour. The resulting product will have a surface area of at least 200 square meters per gram (generally about 200 square meters per gram to about 400 square meters per gram) and a packed density of at least 0.65 g/ml (generally about 0.65 g/ml to about 0.85 g/ml). The product is predominatly (at least about 80%) in the form of eta alumina.

Gel aluminas are X-ray amorphous and are constituted of very small disordered crystals. In particular, the desiccant alumina H-151 is obtained by calcination of such a gel. The sodium content is about 1.0 wt % $Na_2O$ and too high to have good catalytic properties but can be readily decreased to 0.1 wt % with acid solutions. H-151 is no longer manufactured and attempts to reproduce its catalytic properties with alternate starting materials did not succeed.

The use of readily available bayerite as a raw material is another advantage of this invention. Such material is manufactured from sodium aluminate by LaRoche Chemicals.

As described in the following examples, the catalysts made from bayerite have catalytic properties similar to those of H-151. Low soda, high surface area and high packed density lead to their high catalytic activities.

Moreover, it has been found that the impregnation of about 0.2% to about 3%, preferably 2 wt % fluorine on the calcined bayerite doubles its catalytic activity while only small improvements were obtained by impregnating H-151 and gibbsite derived materials.

While the reaction of phenol and aniline is well known and commercialized, it has now been found that amination of other phenols such as p-cresol and xylenol can be readily carried out by our process without any isomerization. For instance, pure p-toluidine can be made from p-cresol without any formation of m-toluidine o-toluidine. Consequently, aromatic amines can now be prepared from their phenolic homologues instead of using nitrobenzene derivatives.

TEST CONDITIONS AND PERFORMANCE DEFINITION

Performance tests conducted to evaluate various catalysts were carried out in a ¾" and 1" O.D. reactor with a catalyst charge of approximately 100 to 250 ml. Ammonia and phenol vapor mixtures were adjusted at a mole ratio of about 18-20 and introduced in the reactor heated at about 365° C. and pressurized at about 240-250 psig. LHSV of phenol was adjusted between 0.04 and 0.08 ml phenol per ml catalyst per hour. As used herein, "LHSV" has the conventional meaning, Liquid Hourly Space Velocity, or liters of liquid feed pumped into the system per liter of catalyst bed per hour. Under these conditions, the plot of phenol conversion versus 1/LHSV is a linear relationship for which the value of the slope is related to an apparent rate constant. That value permits the ranking of catalysts with Varying LHSV. As a comparative example, acid leached H-151 has an apparent rate constant of 3.63. This value has been obtained from example 1 of U.S. Pat. No. 3,860,650 and from reaction tests in our laboratory. This value has been calculated as follows:

H-151 apparent rate
constant = conversion/(1/LHSV)
98.2/(1/0.0375) = 3.63

EXAMPLE 1

An alumina catalyst was prepared by mixing 800 g of bayerite (Versal B), 200 g of Versal 900 (pseudoboehmite) with 300 ml of deionized water containing 20 g of nitric acid. The resulting mix is then used to make 2mm spheres. The spheres are then dried at 100° C. and calcined at 500° C. for 8 hours in a muffle furnace. The results obtained for the reaction of phenol and ammonia are reported in Table 1 below. The ammonia to phenol mole ratio was kept constant at 20/1.

TABLE 1

| Time (hr) | Phenol LHSV | T (°C.) | Pressure (PSIG) | Conversion (wt %) | Selectivities Aniline | DPA |
|---|---|---|---|---|---|---|
| 49 | 0.08 | 362 | 250 | 49.0 | 97.9 | 0.3 |
| 72 | 0.08 | 362 | 250 | 48.0 | 99.5 | 0.1 |
| 175 | 0.04 | 361 | 250 | 98.8 | 99.6 | 0.3 |
| 302 | 0.04 | 363 | 250 | 99.0 | 99.7 | 0.2 |

TABLE 1-continued

| Time (hr) | Phenol LHSV | T (°C.) | Pressure (PSIG) | Conversion (wt %) | Selectivities Aniline | DPA |
|---|---|---|---|---|---|---|
| 494 | 0.04 | 361 | 250 | 98.3 | 99.4 | 0.5 |
| 622 | 0.08 | 390 | 250 | 99.9 | 99.7 | 0.2 |
| 910 | 0.08 | 392 | 250 | 99.9 | 99.6 | 0.3 |
| 1102 | 0.04 | 368 | 250 | 99.9 | 99.4 | 0.4 |
| 1246 | 0.04 | 366 | 250 | 99.9 | 99.4 | 0.4 |
| 1333 | 0.08 | 367 | 250 | 59.4 | 99.7 | 0.1 |
| 1429 | 0.08 | 368 | 250 | 54.1 | 99.6 | 0.2 |

The results obtained at about 362°–367° C. correspond to an apparent rate constant of about 3.9.

EXAMPLE 2

1/16" alumina extrudates were prepared by mixing 300 g of Versal B, 75 g of Versal 900, both obtained from LaRoche Chemicals, with 150 ml of a solution of 0.4M nitric acid. The mix was then extruded and dried at 110° C. for 16 hours. The dried extrudates were calcined in a muffle furnace at 500° C. for 8 hours.

160 ml of extrudates (109 g) were charged in a ⅜" O.D. reactor and tested at a reaction temperature of 365° C., a pressure of 240 psig, a phenol LHSV of 0.04 and an ammonia to phenol mole ratio of 20.

Under these conditions, the conversion averaged about 91% during 168 hours of reaction. This corresponds to an apparent rate constant of 3.64.

EXAMPLE 3

1/16" alumina spheres were prepared by making a mix containing 80 wt % Versal B and 20 wt % Versal 900, followed by spheroidization.

Four samples of the alumina spheres were then made by calcining the dried material at 450°, 500°, 550° and 600° C., respectively. The test results are reported in Table 2.

TABLE 2

| Calcination Temperature | LHSV | Pressure (PSIG) | Conversion | Apparent Rate Constant |
|---|---|---|---|---|
| 450° C. | 0.08 | 240 | 49.2 | 3.93 |
| 500° C. | 0.08 | 240 | 42.0 | 3.36 |
| 550° C. | 0.08 | 240 | 44.0 | 3.52 |
| 600° C. | 0.08 | 240 | 42.0 | 3.36 |

The selectivity to aniline was about 99.4% and the selectivity to diphenylamine was about 0.05%.

EXAMPLE 4

A sample of the alumina of Example 2 was impregnated with fluoride by adsorbing an ammonium bifluoride water solution on it. The loading of F was adjusted at about 2 wt % of the alumina. The impregnated alumina was then calcined in a muffle furnace at 500° C. and subsequently tested for the amination of phenol with a LHSV=0.08, T=365° C. and a system pressure of 250 psig. The phenol conversion was about 85 wt % which corresponds to an apparent rate constant of 6.8 or 1.8 times the apparent rate constant of acid leached H-151 alumina.

EXAMPLE 5

In order to demonstrate the feasibility of making aromatic amines other than aniline, p-cresol was used and fed to the reactor containing the catalyst of Example 1. At 365° C. and LHSV=0.04, all p-cresol was converted to p-toluidine without the formation of m- and o-toluidine.

EXAMPLE 6

3,5 xylenol was also fed under the same conditions as Example 5. Conversion was about 99 wt % and 3,5 xylidine selectivity was bout 99 wt %.

COMPARATIVE EXAMPLE I

An alumina was prepared with Versal 850 (pseudoboehmite) by extrusion and calcination at 550° C. The results of a reaction test identical to Example 2 indicate a conversion of about 55 wt % which corresponds to an apparent rate constant of about 2.2.

COMPARATIVE EXAMPLE II

E-3450 manufactured by Engelhard was tested under the conditions of Example 2 and the conversion of phenol was about 70 wt %. The calculated apparent rate constant was about 2.8.

COMPARATIVE EXAMPLE III

Alcoa CSS-325 1/8" alumina spheres was tested under the conditions of Example 2. The phenol conversion was about 30 wt % and corresponds to an apparent rate constant of about 1.2.

In the amination reaction, we may use pressures from about 100 to about 400 psig, temperatures in the range of 300° to 450° C., LHSVs of 0.03 to about 3, and molar ratios of ammonia to phenolic compound of from 10:1 to about 30:1.

We claim:

1. A vapor phase process for preparing aromatic amines from phenol having 0–2 methyl substitutions and ammonia comprising reacting ammonia and a phenol having 0–2 methyl substitutions in the presence of a catalyst comprising alumina which is predominantly eta alumina and which is made by calcining bayerite at a temperature between about 400° C. and about 600° C., having a surface area of at least 200 sq. meters per gram and having a packed density of at least 0.65 gram per ml.

2. Process of claim 1 wherein the alumina is derived from a mixture containing at least 80 wt. % (of total solids) bayerite and from 1% to about 20 wt. % (of total solids) pseudoboehmite.

3. Process of claim 1 wherein the reaction temperature for the reaction of phenolic compound and ammonia is about 300° C. to about 450° C., the pressure from about 100 to about 400 psig and LHSV from about 0.03 to 0.3.

4. Process of claim 1 wherein the phenol has no methyl substitutions and the aromatic amine is aniline.

5. Process of claim 1 wherein the phenol compound is cresol and the aromatic amine is p-toluidine.

6. Process of claim 1 wherein the phenol compound is 3,5 xylenol and the aromatic amine is 3,5 xylidine.

7. Process of claim 1 wherein the alumina contains about 0.2% to about 3% by weight fluorine.

* * * * *

UNITED STATES PATENT AND TRADEMARK OFFICE
CERTIFICATE OF CORRECTION

PATENT NO.  : 5,214,210
DATED       : May 25, 1993
INVENTOR(S) : Alain A. Schutz and Leonard A. Cullo It is certified that error appears in the above-identified patent and that said Letters Patent is hereby corrected as shown below:

Column 2, line 30, after "Pural", delete "(Condes Chemie)" and substitute

-- (Condea Chemie) --.

Column 4, line 20, before "o-toluidine", insert -- or --.

Signed and Sealed this

Twenty-first Day of December, 1993

Attest:

BRUCE LEHMAN

*Attesting Officer*            *Commissioner of Patents and Trademarks*